United States Patent [19]

Shur

[11] Patent Number: 4,511,558

[45] Date of Patent: Apr. 16, 1985

[54] ALPHA-LACTALBUMIN CONTRACEPTIVE

[75] Inventor: Barry D. Shur, Houston, Tex.

[73] Assignee: University Patents, Inc., Westport, Conn.

[21] Appl. No.: 495,035

[22] Filed: May 16, 1983

[51] Int. Cl.³ .......................... C12Q 1/54; C12Q 1/48; C12N 9/96; A61K 37/00; A61K 31/00; A61K 35/48; A01N 1/02

[52] U.S. Cl. .......................................... 514/8; 424/94; 424/105; 260/112 R; 435/2; 435/14; 435/15; 435/188; 514/843

[58] Field of Search .................. 424/176, 177, 94, 105; 260/112 R; 435/2, 14, 15, 188

[56] References Cited

U.S. PATENT DOCUMENTS

| | | | |
|---|---|---|---|
| 3,876,757 | 4/1975 | Scherm | 424/44 |
| 4,007,087 | 2/1977 | Ericsson | 195/1.8 |
| 4,009,260 | 2/1977 | Ericsson | 424/105 |
| 4,025,129 | 5/1980 | Podolsky et al. | 435/193 |
| 4,153,686 | 5/1979 | Nagel | 424/176 |
| 4,264,575 | 4/1981 | Zimmerman | 424/22 |
| 4,264,576 | 4/1981 | Zimmerman | 424/22 |
| 4,264,577 | 4/1981 | Zimmerman | 424/22 |
| 4,264,578 | 4/1981 | Burck | 424/22 |
| 4,323,548 | 4/1982 | Scherm | 424/44 |

OTHER PUBLICATIONS

Shur, B. D. and Hall, N. G., J. Cell Biol., Nov. 1982, vol. 95, pp. 574–579, "A Role for Mouse Sperm Surface ...".
Aschaffenburg, R., et al., *Bioch.*, 65:273–277, (1957).
Brinster, R. L., *J. Exp. Zool.*, 158:59–68, (1965).
Brodbeck, U., et al., *J. Biol. Chem.*, 242:1391–1397, (1967).
Brown, R. C., et al., *Biochimica et Biophysica Acta*, 491:82–92, (1977).
Buttar, H. S., *Toxicol. Letters*, 13:211–216, (1982).
Castellino, F. J., et al., *J. Biol. Chem.*, 245:417–424, (1970).
Cervone, F., et al., *Biochimica et Biophysica Acta*, 295:555–563, (1973).
Chvapil, M., et al., *Fertility and Sterility*, 33:445–449, (1980).
Chvapil, M., et al., *Contraception*, 22:325–339, (1980).
Findlay, J. B. C., et al., *Eur. J. Biochem.*, 27:65–86, (1972).
Hamilton, D., *Biol. of Reproduction*, 25: 385–392, (1981).
Jick, H., et al., *JAMA*, 245: 1329–1332, (1981).
Jones, R., et al., *Biochem. J.*, 206: 161–164, (1982).
Kuwajima, K., et al., *J. Mol. Biol.*, 106:359–373, (1976).
Prasad, R., et al., *J. Biol. Chem.*, 255:5834–5837, (1980).
Robbins, F. M., et al., *Biochim. Biophys. Acta*, 82:186–188, (1964).
Shapiro, S., et al., *JAMA*, 247: 2381–2384, (1982).
Shur, B., *The Glycoconjugates*, vol. III, M. Horowitz ed., Academic Press, NY, pp. 145–185, (1982).
Shur, B., et al., *J. Cell Biol.*, 95: 567–573, (1982).
Zaneveld, L. et al., *FEBS Letters*, 11: 345–347, (1970).
Zatuchni, G., et al., eds. *Research Frontiers in Fertility Regulation*, pp. 1–328, Harper & Row, 1980.
Zatuchni, G. et al., eds., *Vaginal Contraception: New Developments*, pp. 1–280, Harper & Row, 1979.

*Primary Examiner*—Thomas G. Wiseman
*Assistant Examiner*—Robin Lyn Teskin
*Attorney, Agent, or Firm*—Barbara A. Shimei; Maurice M. Klee

[57] ABSTRACT

A contraceptive agent is provided which comprises biologically-active alpha-lactalbumin. The agent can be administered to female mammals using a variety of pharmaceutically acceptable vehicles, provided the alpha-lactalbumin retains its biological activity in the presence of the vehicle.

6 Claims, 4 Drawing Figures

ALPHA-LACTALBUMIN CONTRACEPTIVE

The invention described herein was made in the course of work partly supported by Grant Number HD15856 from the National Institutes of Health, Department of Health and Human Services.

BACKGROUND OF THE INVENTION

1. Field of the Invention

This invention relates to contraceptive compositions and in particular to a contraceptive composition which includes biologically-active alpha-lactalbumin.

2. Description of the Prior Art

The search for effective contraceptives has been going on for literally thousands of years. Among the contraceptive methods presently in general use are oral contraceptives, intrauterine devices, diaphragms, condoms and various vaginal spermicides administered in the form of jellies, creams, foams, foaming tablets, suppositories and soluble films. As is commonly known, each of these contraceptive methods has disadvantages for particular individuals or for all individuals when used over an extended period of time. For example, the use of oral contraceptives, the most popular form of contraceptive at the present time, has been associated with nausea, depression, weight gain and headache, as well as an increased long-term risk of stroke, myocardial infarction, thromboembolia and hypertension.

In particular, the vaginal spermicides have come under increasing criticism because of the absorption and subsequent effects of the chemicals used in such preparations on various female tissues and organs. The spermicide most commonly used today in such preparations is the nonionic detergent nonylphenoxypolyethyleneoxyethanol (nonoxynol 9). Numerous studies have been done on the absorption of nonoxynol 9 by the vaginal epithelium. See, for example, Buttar, H. S., "Transvaginal Absorption and Disposition of Nonoxynol-9 in Gravid Rats", *Toxicology Letters*, Vol. 13, 1982, pages 211–216; Chvapil, M., Droegemueller, W., Owen, J. A., Eskelson, C. D., Betts, K., "Studies of Nonoxynol-9. I. The Effect on the Vaginas of Rabbits and Rats", *Fertility and Sterility*, Vol. 33, No. 4, April 1980, pages 445–449; Chvapil, M., Eskelson, C. D., Droegemueller, W., Ulreich, J. B., Owen, J. A., Ludwig, J. C., Stiffel, V. M., "New Data on the Pharmacokinetics of Nonoxynol 9", in *Vaginal Contraception: New Developments*, Zatuchni et al. editors, Harper & Row, Hagerstown, Md., 1979, pages 165–174; Chvapil, M., Eskelson, C. D., Stiffel, V., Owen, J. S., and Droegemueller, W., "Studies on Nonoxynol-9. II. Intravaginal Absorption, Distribution, Metabolism and Excretion in Rats and Rabbits", *Contraception*, September 1980, Vol. 22, No. 3, pages 325–339; Jick, H., Walker, A. M., Rothman, K. J., Hunter, J. R., Holmes, L. B., Watkins, R. N., D'Eward, D. C., Danford, A., Madsen, S., "Vaginal Spermicides and Congenital Disorders", *JAMA*, Apr. 3, 1981, Vol. 245, No. 13, pages 1329–1332; and Shapiro, S., Slone, D., Holnonon, O. P., Kaufman, D. W., Rosenberg, L., Mitchell, A. A., Helmrich, S. P., "Birth Defects and Vaginal Spermicides", *JAMA*, May 7, 1982, Vol. 247, No. 17, pages 2381–2384.

Although the results of these studies are not without controversy, there seems to be general agreement that nonoxynol 9 is rapidly taken up by the vaginal epithelium, enters the circulation, and accumulates in the liver, among other tissues. Biochemical and morphological studies have documented abnormalities in these tissues as a result of nonoxynol 9 administration. Moreover, the detergent can be found in the milk of lactating rats and in the serum of their pups within two hours after an intravaginal application. Further, although very controversial, some studies have suggested an association of congenital abnormalities with the use of nonoxynol 9 as a spermicidal agent. See "Vaginal Spermicides and Congenital Disorders" and "Birth Defects and Vaginal Spermicides", supra.

SUMMARY OF THE INVENTION

In view of the present state of the art as described above, it is evident that more acceptable contraceptive methods and, in particular, substitutes for the active ingredients of presently used vaginal spermicides are needed.

It is an object of the present invention to provide such an improved contraceptive composition. In particular, it is an object of the present invention to provide a contraceptive composition which is more biologically compatible and acceptable than contraceptive compositions previously used. Moreover, it is an object of this invention to provide a contraceptive composition based on a naturally occurring material which has specific contraceptive effects and a minimum of adverse side effects. It is a further object of the invention to provide a contraceptive composition which is inexpensive and based on a material which is commercially available in purified form.

As discussed in detail below in connection with the preferred embodiments of the invention, it has been found that these and other objects of the invention are achieved by employing biologically-active alpha-lactalbumin as a contraceptive agent.

Alpha-lactalbumin is one of the major protein constituents of milk. It is produced by a variety of species of mammals, and, in particular, it is found in human and bovine milk. As such, it is a natural product which is biologically compatible and acceptable as evidenced by the fact that it is fed to infants during nursing.

Furthermore, as described in detail below, various methods are known for purifying alpha-lactalbumin while maintaining its biological activity. Accordingly, at the present time, biologically-active alpha-lactalbumin suitable for use in accordance with the present invention is commercially available from a number of sources at reasonable prices.

That alpha-lactalbumin, a milk protein, can function as a contraceptive is indeed surprising. Yet, as described in detail below, biologically-active alpha-lactalbumin has been found by both in vitro and in vivo tests to be an effective contraceptive agent. Unlike prior art contraceptive agents, such as nonoxynol 9, alpha-lactalbumin does not function by killing sperm. Although not wishing to be bound by any particular mode of operation, it is believed that in vivo biologically-active alpha-lactalbumin functions as a contraceptive by one or a combination of the following mechanisms: interfering with the binding of sperm and egg; interfering with the implantation of fertilized eggs; or altering the motility of sperm. Because none of these mechanisms involve using a toxic agent to kill sperm, alpha-lactalbumin does not have the numerous adverse side effects which accompany toxic agents whose mode of operation is to kill living matter, i.e., sperm. It is because alpha-lactalbumin is not a killing agent but surprisingly does function as a contraceptive agent, that alpha-lactalbumin satisfies both the object of preventing conception and the object of having minimum side effects.

In the description of the preferred embodiments presented below, specific examples of the use of biologically-active alpha-lactalbumin to prevent conception are presented. It is to be understood that these examples are not intended to limit the present invention in any way and that the scope of the invention covers all uses of biologically-active alpha-lactalbumin as a contraceptive agent.

As used herein, the words "contraceptive", "contraceptive agent", and "contraception" are used in their broadest sense to encompass the concept of preventing full-term pregnancy. Also, the expression "biologically-active alpha-lactalbumin" is used to describe alpha-lactalbumin which is capable of changing the specificity of the enzyme galactosyltransferase away from N-acetylglucosamine (see discussion of effect of alpha-lactalbumin on galactosyltransferase, infra).

DESCRIPTION OF THE PREFERRED EMBODIMENTS

Figure 1:
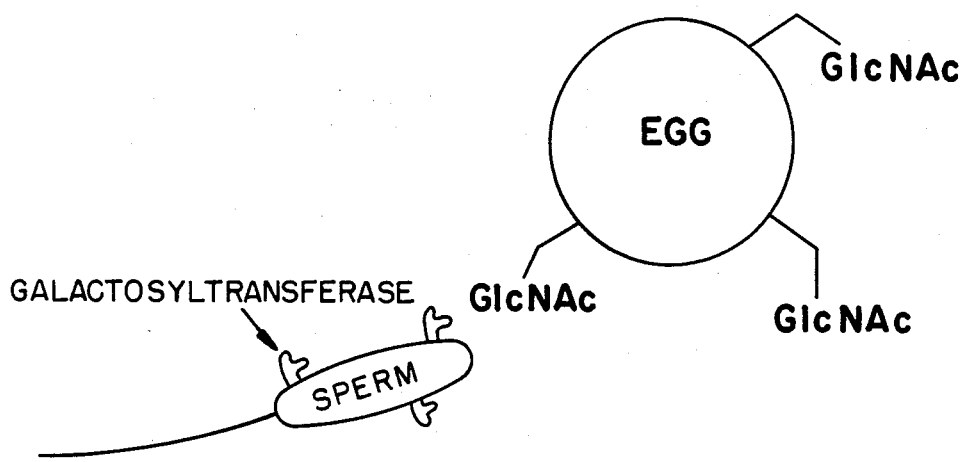
FIG. 1 is a schematic diagram illustrating one mechanism by which biologically-active alpha-lactalbumin is believed to function in vivo as a contraceptive agent in accordance with the present invention.

As discussed above, the present invention relates to the use of biologically-active alpha-lactalbumin as a contraceptive agent. The biologically-active alpha-lactalbumin for use in the present invention can be derived from a variety of milk sources including human, cow, goat, rat and other mammalian milks.

Alpha-lactalbumin is a well-characterized milk protein, having a relatively low molecular weight in comparison with other milk proteins. See, for example, Findlay, J. B. C. and Brew, K., "The Complete Amino-Acid Sequence of Human alpha-Lactalbumin", Eur. J. Biochem., Vol. 27, 1972, pages 65–86; and Kuwajima, K., Nitta, K., Yoneyama, M., and Sugai, S., "Three-state Denaturation of alpha-Lactalbumin by Guanidine Hydrochloride", J. Mol. Biol., Vol. 106, 1976, pages 359–373. This lower molecular weight allows alpha-lactalbumin to be rapidly and simply purified from milk, using salt fractionation, acid precipitation and gel chromatography.

Standard procedures for the purification of alpha-lactalbumin, which yield about 1 gram of pure alpha-lactalbumin per liter of milk, are well known. Examples of such procedures can be found in the following references, the pertinent portions of which are incorporated herein by reference: Aschaffenburg, R., and Drewry, J., "Improved Method for the Preparation of Crystalline beta-Lactoglobulin and alpha-Lactalbumin from Cow's Milk", Bioch., 1957, Vol. 65, pages 273–277; Brodbeck, U., Denton, W. L., Tanahashi, N., and Ebner, K. E., "The Isolation and Identification of the B Protein of Lactose Synthetase as alpha-Lactalbumin", The Journal of Biological Chemistry, 1967, Vol. 242, No. 7, pages 1391–1397; Brown, R. C., Fish, W. W., Hudson, B. G., and Ebner, K. E., "Isolation and Characterization of Rat alpha-Lactalbumin: A Glycoprotein", Biochimica et Biophysica Acta, 1977, Vol. 491, pages 82–92; Castellino, F. J., and Hill. R. L., "The Carboxymethylation of Bovine alpha-Lactalbumin", The Journal of Biological Chemistry, 1970, Vol. 245, No. 2, pages 417–424; Cervone, F., Diaz Brito, J., Di Prisco, G., Garofano, F., Gutierrez Norona, L., Traniello, S., and Zito, R., "Simple Procedures For The Separation And Identification of Bovine Milk Whey Proteins", Biochimica et Biophysica Acta, 1973, Vol. 295, pages 555–563; Prasad, R., and Ebner, K. E., "Charge Forms of Wistar Rat alpha-Lactalbumin", The Journal of Biological Chemistry, 1980, Vol. 255, No. 12, pages 5834–5837; and Robbins, F. M., and Kronman, M. J., "A Simplified Method for Preparing alpha-Lactalbumin and beta-Lactoglobulin from Cow's Milk", Biochim. Biophys. Acta, 1964, Vol 82, pages 186–188.

As described in these references, alpha-lactalbumin is generally prepared by first preparing a crude lactalbumin preparation from either raw or skim milk by ammonium sulfate fractionation. Such crude lactalbumin is commercially available and is commonly used as an inexpensive source of protein. Since the alpha-lactalbumin in the commercially available crude preparations is typically denatured and thus rendered biologically inactive, these crude preparations cannot normally be used in the practice of the present invention.

To obtain biologically-active alpha-lactalbumin from the crude lactalbumin preparation, the salt fractionation step is typically followed by acid precipitation and one-step gel chromatography, usually using Sephadex G-100 or Bio-Gel P-30 or P-150. Pure, biologically-active alpha-lactalbumin prepared in this way is available as a dry powder from Gallard-Schlesinger Chemicals, Carle Place, N.Y. (catalog no. 44171) and from Sigma Chemical Company, St. Louis, MO (catalog nos. L5385 and L6010). In the experiments described below, Sigma L6010 biologically-active alpha-lactalbumin was used.

Once obtained, the biologically-active alpha-lactalbumin can be administered in a variety of ways presently known to the art or which may be developed in the future. As discussed briefly above and in more detail below, biologically-active alpha-lactalbumin is believed to perform its contraceptive function by one or a combination of mechanisms including interfering with the union of sperm and egg, preventing the implantation of fertilized eggs in the uterine wall, or altering the motility of sperm. Accordingly, to be effective, the biologically-active alpha-lactalbumin must be introduced and dissolved in either the vaginal or uterine fluids. Numerous methods for such introduction are well known in the art. A recent review of some of these methods can be found in Vaginal Contraception: New Developments, edited by G. I. Zatuchni, A. J. Sobrero, J. J. Speidel, and J. J. Sciarra, Harper and Row, Hagerstown, Md., 21740, 1979. Methods for introducing contraceptive agents into the uterus or vagina and thereafter slowly releasing the contraceptive agent can be found in U.S. Pat. Nos. 4,264,575, 4,264,576, 4,264,577 and 4,264,578. Such methods can be used with the present invention, as well as other methods for releasing biologically-active alpha-lactalbumin over time. Such methods of introduction described in the review and patents cited hereinabove are incorporated herein by reference.

In the examples presented below, a simple vehicle for administrating biologically-active alpha-lactalbumin consisting of Dulbecco's Modified Eagle Medium (Gibco Co., Grand Island, N.Y.) and K-Y lubricating jelly (Johnson and Johnson, Inc., New Brunswick, N.J.) has been used. It is to be understood that this particular vehicle was chosen for experimental purposes only and is in no way limiting with regard to the types of vehicles or methods of administration to be employed in practicing the present invention. For example, pharmaceutically acceptable vehicles which do not deactivate alpha-lactalbumin include collagen and polyurethane sponges which are inert with respect to biologically-active alpha-lactalbumin. In particular, a polyuethane sponge of the type used in the TODAY sponge manufactured by Vorhauer Laboratories, Inc., Costa Mesa, Calif., can be used in the practice of the present invention. Other vehicles suitable for use with the present invention include intravaginal contraceptive membrane suppositories composed of inert materials which will not deactivate alpha-lactalbumin, such as agarose, dextran or cellulose polymer gels. Similarly, vaginal rings composed of inert materials can be used to administer the biologically-active alpha-lactalbumin.

Although the biologically-active alpha-lactalbumin can be administered in a variety of ways, it is important that the method and vehicle chosen for administration is such that the alpha-lactalbumin is not deactivated. In particular, materials which will denature alpha-lactalbumin must be avoided. For example, certain formulations of contraceptive foams include surfactants of the type which are capable of denaturing alpha-lactalbumin, thus destroying its contraceptive effect. Examples of such foams appear in U.S. Pat. Nos. 3,876,757 and 4,323,548. These patents describe contraceptive compositions which include such ionic surfactants as sodium lauryl sulfate and sodium lauryl ether sulfate. These surfactants will denature alpha-lactalbumin and thus the contraceptive administration vehicles described in U.S. Pat. Nos. 3,876,757 and 4,323,548 are not of the type which can be used with the present invention.

Except for the specific requirement that the vehicle and method used to administer alpha-lactalbumin not be of the type which will deactivate the alpha-lactalbumin, a variety of methods and vehicles for application can be used. Thus, the biologically-active alpha-lactalbumin can be administered in the forms of pharmaceutically acceptable, non-deactivating gels, jellies, pastes, foams, suppositories, soluble films or carriers, or in conjunction with sponges, vaginal rings, intrauterine devices, diaphragms and the like.

Although not wishing to be bound by any particular theory of operation, it is believed that biologically-active alpha-lactalbumin produces its contraceptive effects in vivo by one or a combination of the following mechanisms.

As is well known, the first critical event to occur during fertilization is the fusion of sperm and egg. It is believed that in vivo fusion is mediated by specific complementary cell surface molecules which interact with one another in a "lock and key" fashion. In particular, it is believed that one of the sperm surface molecules which interact in the lock and key fashion is the enzyme galactosyltransferase, which specifically binds to N-acetylglucosamine residues (GlcNAc) on the egg's surface. FIG. 1 schematically shows this interaction between the galactosyltransferase on the surface of the sperm and the N-acetylglucosamine residues on the egg surface.

Galactosyltransferase normally transfers galactose to N-acetylglucosamine to produce N-acetyllactosamine (galactose-GlcNAc). However, in the presence of alpha-lactalbumin, galactosyltransferase preferentially binds to glucose (Glc) rather than N-acetylglucosamine, the result being the synthesis of the milk sugar lactose (galactose-Glc), rather than N-acetyllactosamine.

It is believed that at least one mechanism responsible for the in vivo contraceptive effect of alpha-lactalbumin involves this change in galactosyltransferase binding specificity dictated by biologically-active alpha-lactalbumin. That is, in the absence of biologically-active alpha-lactalbumin, the galactosyltransferase on the surface of the sperm preferentially binds to the N-acetylglucosamine residues on the egg surface producing fusion between the sperm and the egg. In the presence of biologically-active alpha-lactalbumin, however, galactosyltransferase no longer preferentially binds to N-acetylglucosamine, thus preventing fusion of sperm and egg.

As described in detail below, biologically-active alpha-lactalbumin interfers with sperm-egg binding at low concentration levels. For example, a concentration of alpha-lactalbumin of 2% by weight per volume of medium has been found to reduce the number of sperm bound per egg by 92%. Accordingly, concentration levels of biologically-active alpha-lactalbumin in the uterine or vaginal fluids can effectively range from about 1% to about 10% (w/v) to produce the contraceptive effect of the present invention. Since the uterine and vaginal volumes of warm blooded female mammals can vary significantly, e.g., from about 0.05 ml to about 5.0 liters, it is therefore necessary to administer the biologically-active alpha-lactalbumin in dosage units varying from about 0.5 mg to about 500 grams in order to obtain the desired concentration levels in the uterine or vaginal fluids.

The presence of glucose, N-acetylglucosamine or similar sugars such as myo-inositol in the medium strengthens the binding of alpha-lactalbumin to galactosyltransferase, thus increasing the efficiency of alpha-lactalbumin's action on galactosyltransferase. Accordingly, to the extent such sugars are not present in the normal vaginal and uterine fluids, they should be supplemented by means of the vehicle used to administer the biologically-active alpha-lactalbumin. Sufficient sugar should be administered to produce a final concentration in the vaginal or uterine fluids on the order of 10–50 mM. In view of the vaginal and uterine volumes discussed above and the fact that sugars such as glucose and N-acetylglucosamine have molecular weights around 200 grams/mole, the sugar dosage units required to produce the desired concentrations of 10–50 mM vary from about 0.1 mg to about 50 grams.

Another possible mechanism by which alpha-lactalbumin functions as a contraceptive agent in vivo involves prevention of embryonic implantation into the uterine endometrium. Again, it is believed that biologically-active alpha-lactalbumin functions by interacting with and modifying surface galactosyltransferase, in this case galactosyltransferase on the surface of the embryo rather than on the surface of the sperm. In accordance with this mechanism of operation, biologically-active alpha-lactalbumin serves as a contraceptive agent even after fertilization has occurred because it prevents full-term pregnancy early in gestation by causing implantation failure.

In addition to the foregoing mechanisms, it is believed that biologically-active alpha-lactalbumin also has an effect on the motility of sperm. Prior to the time of fertilization, sperm have the ability to move from one place to another without deviating from their course. At the time of fertilization, sperm normally lose this ability, that is, they still can move but now they do deviate from their course. Biologically-active alpha-lactalbumin is believed to interfere with the process by which sperm normally lose the ability to move from one place to another without deviations at the time of fertilization, and this also may be one of the mechanisms responsible for the contraceptive effects exhibited by biologically-active alpha-lactalbumin in vivo.

As illustrated by the examples to which we now turn, the combined effect of the foregoing mechanisms, as well as possibly other unknown mechanisms, is to produce a striking contraceptive effect under both in vitro and in vivo conditions.

EXAMPLE 1

Effect Of Alpha-Albumin On Sperm-Egg Binding

This example shows the significant decrease in the number of sperm bound per egg caused by biologically-active alpha-lactalbumin. The example also shows that a concentration of 2% (w/v) of biologically-active alpha-lactalbumin is sufficient to reduce the number of sperm bound per egg by 92%. The experimental data is plotted in FIG. 2.

The data for this example was obtained in the following manner. Eggs were isolated from superovulated CD1 females (Charles River Breeding Laboratories, Inc., Wilmington, MA.) in a modified complete medium (CM), minus lactose, plus 5.6 mM fructose. See Brinster, R. L., "Studies on the development of mouse embryos in vitro. II. The effect of energy source", *J.Exp.Zool.*, Vol. 158, 1965, pages 59–68. The eggs were freed from the surrounding cumulus cells with 0.1% hyaluronidase (Sigma Chemical Co., St. Louis, MO) (23° C., 10 min), and then washed three times in CM.

Viable sperm were removed from minced cauda epididymides of CD1 males and capacitated in CM for 1 hr in a 37° C., 7% $CO_2$ tissue-culture incubator. The sperm concentration and motility were determined with a hemocytometer. 40 microliter aliquots of capacitated sperm were added to aproximately 30 cumulus-free eggs in 400 microliters of CM, having varying concentrations of biologically-active alpha-lactalbumin (Sigma L6010), under mineral oil. Within any one set of assays, on a given day, control and experimental incubations were prepared from a common sperm suspension. In this way, sperm concentration and motility were identical in all cultures, thus eliminating inevitable variations between males sacrificed on different days. Sperm binding to the zona pellucida portion of the eggs was proportional to the final sperm concentration from $1-5 \times 10^5$ sperm/ml. Assays usually contained $3 \times 10^5$ sperm/ml final concentration, of which more than 50% were motile.

In some experiments, the cultures were incubated in a reciprocating (30 reciprocations/min), 37° C. water bath; while in other assays, the cultures were incubated in a stationary 37° C., 7% $CO_2$ tissue-culture incubator. Results were qualitatively the same under both incubation conditions.

After 20 min of incubation, the entire 440 microliter suspension was applied to the top of a discontinuous microgradient composed of 50 microliters of CM, 25 microliters of 1.8% dextran, and 25 microliters of 2.25% dextran containing 2.5% glutaraldehyde. The gradient was centrifuged for 90 seconds at 100 g, sedimenting the eggs with adhering sperm into the glutaraldehyde-containing dextran layer. Unbound sperm partitioned in the CM and adjacent 1.8% dextran layers. The egg pellets were removed and the number of sperm bound/egg was counted using phase-contrast microscopy.

Figure 2:
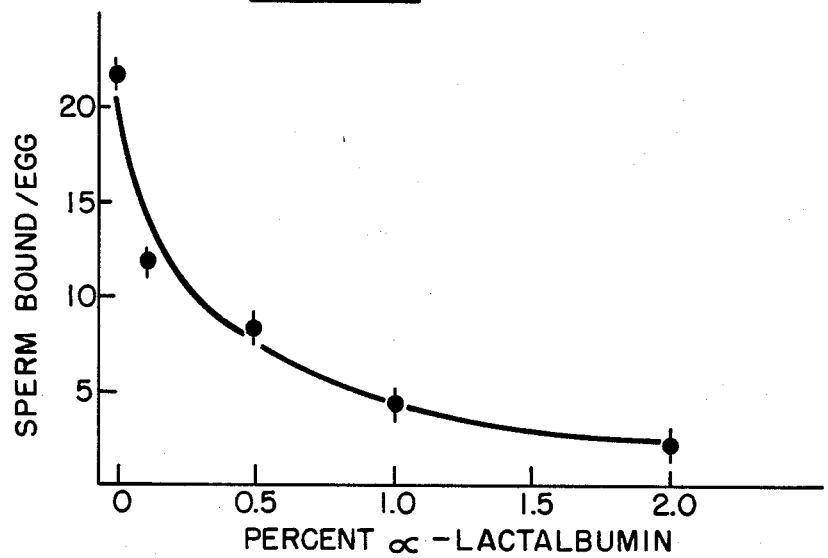
FIG. 2 is a graph showing the number of sperm bound to an egg as a function of the concentration of biologically-active alpha-lactalbumin in the surrounding medium.

The results of these experiments are shown in FIG. 2 where the error bars represent ±SEM (standard error of the mean). As shown in this figure, when alpha-lactalbumin was added to in vitro fertilization assays containing capacitated sperm, sperm binding to the zona pellucida portion of the egg was inhibited in a dose-dependent manner. Half-maximal inhibition was seen at 0.1% alpha-lactalbumin (69 micromolar). Two percent alpha-lactalbumin inhibited sperm binding by 92%.

Glucose and GlcNAc (5 mM each) were present throughout these assays to ensure efficient binding of the alpha-lactalbumin to the galactosyltransferase. These levels of free sugar had little inhibitory effect by themselves on sperm-zona binding. To accurately assess the effect of alpha-lactalbumin, the assays were conducted in the absence of bovine serum albumin (BSA).

It was determined that the inhibition of sperm binding to the egg by alpha-lactalbumin was not the result of simply adding protein, since BSA additions (including free sugar) over the same dose range actually enhanced binding, but by insignificant levels (0% BSA, 18.8±1.8 sperm/egg; 0.1% BSA, 19.5±1.6 sperm/egg; 2% BSA, 21.8±1.5 sperm/egg). Also, under the experimental conditions used, the effects of alpha-lactalbumin could not be attributed to any changes in sperm motility.

In sum, this series of in vitro tests show that biologically-active alpha-lactalbumin strongly inhibits sperm-egg binding at low concentration levels in a dose-dependent manner.

EXAMPLE 2

Biologically-Active versus Biologically-Inactive alpha-Lactalbumin

This example shows that biologically-active alpha-lactalbumin, as opposed to deactivated alpha-lactalbumin, must be used to achieve the contraceptive function of the present invention.

Three comparative tests were run using the sperm-egg binding methodology described in Example 1. In the first test, 2% BSA was incorporated into the incubation medium; in the second test, 2% biologically-active alpha-lactalbumin was used; and in the third test, 2% boiled alpha-lactalbumin, i.e., denatured and thus deactivated alpha-lactalbumin, was used. The boiled alpha-lactalbumin was of the same type as the biologically-active alpha-lactalbumin (Sigma L6010), but prior to incorporation in the incubation medium, a 10% stock solution was boiled for 10 minutes, and diluted with fresh incubation medium to produce a final concentration of 2%.

Figure 3:
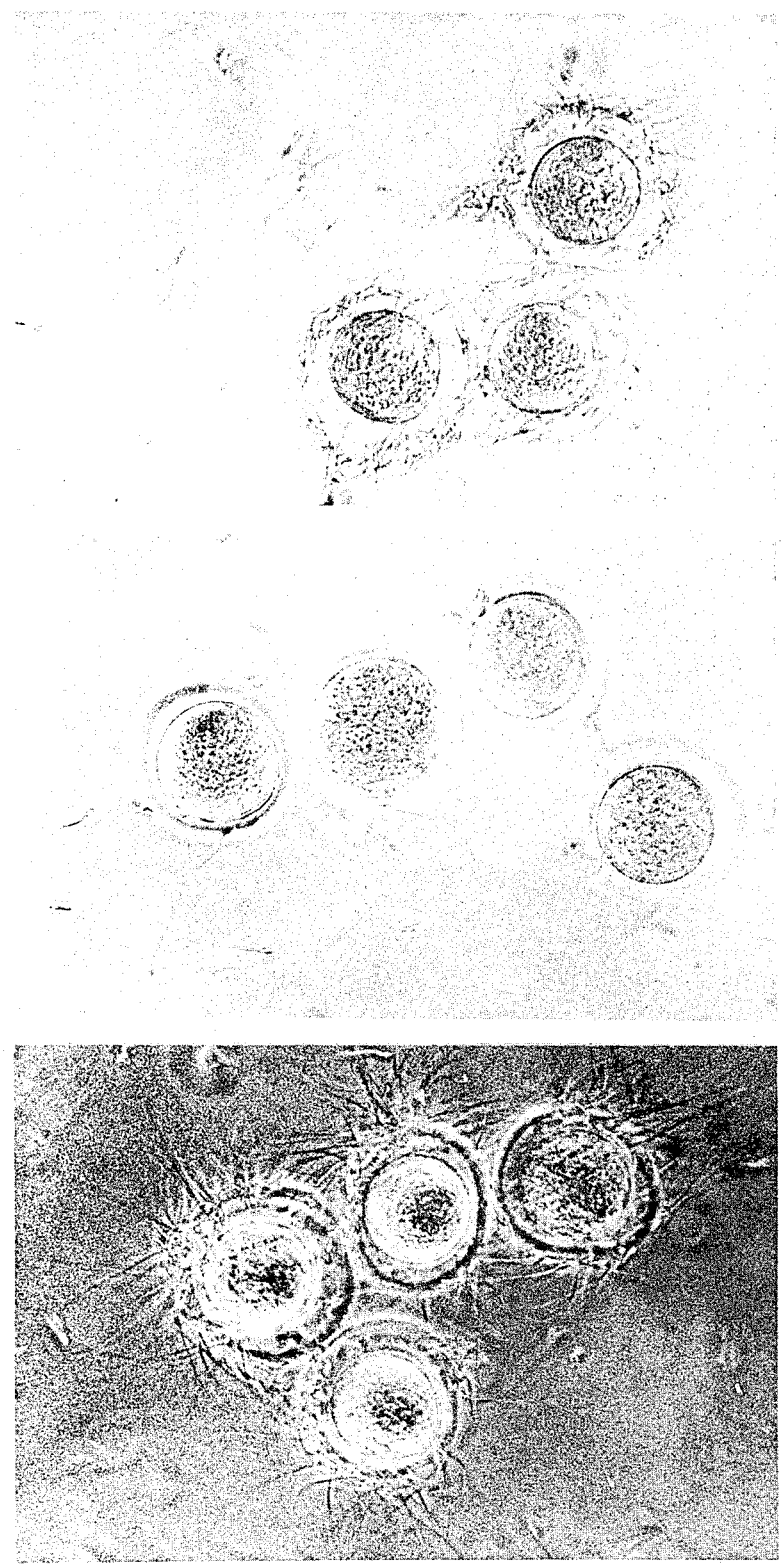
FIG. 3 are photographs taken through a phase-contrast microscope showing the extent of sperm binding to eggs under a control condition (panel labeled "BSA"), in the presence of 2% biologically-active alpha-lactalbumin (panel labeled "α-LA"), and in the presence of 2% alpha-lactalbumin which is not biologically-active (panel labeled "boiled α-LA").

FIG. 3 shows three photographs taken through a phase-contrast microscope of eggs after 20 minutes of incubation under the three test conditions. As shown in this figure, both the 2% BSA (panel labeled "BSA") and the boiled 2% alpha-lactalbumin (panel labeled "boiled α-LA") show numerous sperm bound to the egg. In stark contrast, the 2% biologically-active alpha-lactalbumin preparation (panel labeled "α-LA") shows just a few and in some cases, no sperm bound to the eggs. Accordingly, with BSA or boiled alpha-lactalbumin, fertilization is likely to occur; while with biologically-active alpha-lactalbumin, fertilization is unlikely to occur.

EXAMPLE 3

In Vivo Effect of Biologically-Active alpha-Lactalbumin

This example shows the in vivo contraceptive effects of biologically-active alpha-lactalbumin. The results are shown graphically in FIG. 4 in terms of the change in the distribution of the number of embryos per female for control females and for females which have been treated with biologically-active alpha-lactalbumin prior to mating.

The data shown in FIG. 4 was obtained as follows. A contraceptive composition including biologically-active alpha-lactalbumin was prepared by dissolving 20% alpha-lactalbumin (Sigma L6010) in Dulbecco's Modified Eagle Medium (DME) (Gibco Co., Grand Island, N.Y.) adjusting the pH to 7.2 with 1N NaOH, and mixing the alphalactalbumin/DME mixture with an equal volume of K-Y lubricating jelly (Johnson & Johnson, Inc., New Brunswick, N.J.) to give a final concentration of 10% biologically-active alpha-lactalbumin, 40% Dulbecco's Modified Eagle Medium and 50% K-Y jelly.

The biologically-active alpha-lactalbumin containing contraceptive composition was applied to female mice in the following manner. CD1 female mice (Charles River Breeding Laboratories, Inc., Wilmington, MA), 8–10 weeks of age, were housed individually with CD1 males after the fourth hour of a nine hour dark cycle. After 45 minutes, the females received intravaginally 50 microliters of the biologically-active alpha-lactalbumin/DME/K-Y jelly suspension, and the females were put back in the male's cage for an additional 45 minutes. After this time, the females were removed, checked for a vaginal plug indicating successful mating and housed separately. On the ninth day of gestation, all plugged mice were sacrificed and the number of implantation sites within each uterine horn was determined.

Control mice were handled identically to the experimental mice except that they received an intravaginal application of 50 microliters of 10% bovine serum albumin, 40% DME and 50% K-Y jelly, or alternatively, 50% DME and 50% K-Y jelly. No difference was noted between those control mice which received bovine serum albumin and those which did not receive it.

Figure 4:
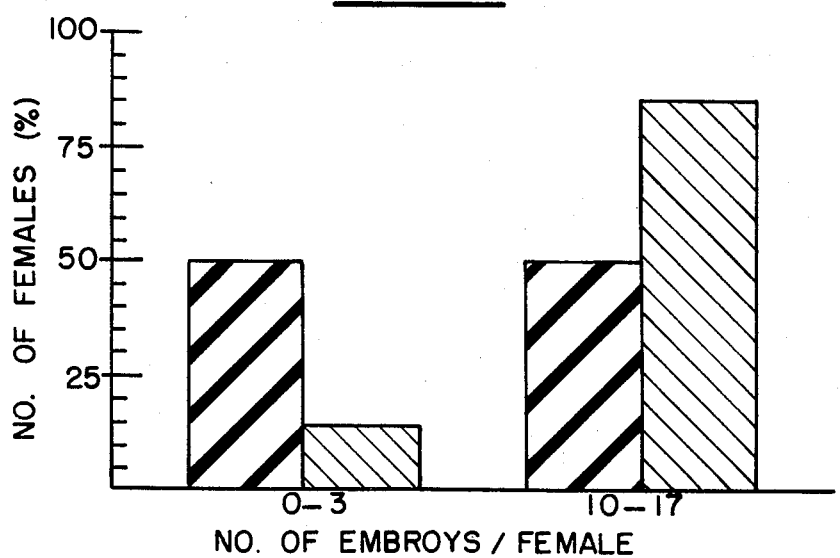
FIG. 4 shows the in vivo contraceptive effect of biologically-active alpha-lactalbumin, wherein the light cross-hatched bars show the distribution of the number of embryos per female mouse for control females and the heavy cross-hatched bars show the same distribution where the female mice have been treated with biologically-active alpha-lactalbumin prior to mating.

The data shown in FIG. 4 represents the results of 20 female mice which were treated with biologically-active alpha-lactalbumin and 22 control mice. The 20 treated mice had a total of 127 embryos giving an average of 6.35 embryos per female. In comparison, the 22 control mice had a total of 240 embryos, giving an average 10.91 embryos per female. That is, on average, the control mice had 72% more embryos that the treated mice.

FIG. 4 shows in more detail the changes in fertility caused by the administration of biologically-active alpha-lactalbumin. As shown in this figure, the control animals (light cross-hatched bars) had essentially a single modal distribution, with 86% of the control animals having between 10 and 17 embryos per female. In contrast, the treated animals (heavy cross-hatched bars) had a bimodal distribution with 50% of the animals having between 0 and 3 embryos per female and 50% having between 10 and 17 embryos per animal. During the experiments, it was noted that the alpha-lactalbumin/DME/K-Y jelly suspension tended to leak out of the vaginas of the treated animals. Accordingly, it is believed that a large percentage of the treated animals having between 10 and 17 embryos per female represents animals for which the contraceptive composition was no longer in place at the time of mating. Therefore, with a vehicle not subject to this leakage phenomenon, an even greater skew of the distribution towards low numbers of embryos will be achieved.

It is to be understood that the foregoing detailed description is given merely by way of illustration and that many variations thereof may be made without departing from the spirit and scope of the invention. In particular, vehicles other than that used above to illustrate the invention can be used to administer the biologically-active alpha-lactalbumin provided the alpha-lactalbumin retains its activity in the presence of the vehicle. Also, in addition to administration in the uterus and the vagina, the biologically-active alpha-lactalbumin can be administered in the oviduct where union of egg and sperm occurs in mammals.

What is claimed is:

1. A contraceptive composition suitable for introduction into the reproductive tract of a female mammal comprising a contraceptively effective amount of biologically-active alpha-lactalbumin contained in a biocompatible carrier material which will not de-activate the alpha-lactalbumin and which is suitable for administering the alpha-lactalbumin to the female mammal's reproductive tract in amounts sufficient to induce contraception.

2. The contraceptive composition of claim 1 further comprising one or more sugars selected from the group consisting of glucose, N-acetylglucosamine and myo-inositol.

3. The contraceptive composition recited in claim 2 wherein the contraceptively effective amount is that which produces an alpha-lactalbumin concentration in at least a portion of the reproductive tract of between approximately one and ten percent weight per volume and wherein the amount of the one or more sugars in the contraceptive composition is sufficient to produce a concentration of the sugar or sugars in at least a portion of the reproductive tract of between approximately ten and fifty millimolar.

4. A method of inducing contraception in a female mammal by introducing into the reproductive tract of said mammal a contraceptive composition which comprises a contraceptively effective amount of biologically-active alpha-lactalbumin contained in a biocompatible carrier material which will not de-activate the alpha-lactalbumin and which is suitable for administering the alpha-lactalbumin to the female mammal's reproductive tract in amounts sufficient to induce contraception.

5. The method of claim 4 wherein the contraceptive composition includes one or more sugars selected from the group consisting of glucose, N-acetylglucosamine and myo-inositol.

6. The method of claim 5 wherein the contraceptively effective amount is that which produces an alpha-lactalbumin concentration in at least a portion of the reproductive tract of between approximately one and ten percent weight per volume and wherein the amount of the one or more sugars in the contraceptive composition is sufficient to produce a concentration of the sugar or sugars in at least a portion of the reproductive tract of between approximately ten and fifty millimolar.

* * * * *